United States Patent [19]

Nagpal

[11] Patent Number: 4,473,393
[45] Date of Patent: * Sep. 25, 1984

[54] PESTICIDAL THIOHYDANTOIN COMPOSITIONS

[75] Inventor: Krishen L. Nagpal, Williamsville, N.Y.

[73] Assignee: Buffalo Color Corporation, West Paterson, N.J.

[*] Notice: The portion of the term of this patent subsequent to Aug. 7, 2001 has been disclaimed.

[21] Appl. No.: 406,008

[22] Filed: Aug. 6, 1982

[51] Int. Cl.³ .................... A01N 43/50; C07D 233/86
[52] U.S. Cl. .................................. 71/92; 424/273 R; 548/312; 548/313; 548/314
[58] Field of Search .................. 548/312, 313, 314; 424/273 R; 71/92

[56] References Cited

U.S. PATENT DOCUMENTS 3,668,217  6/1972  Fujinami et al. .................... 548/314
3,798,233  3/1974  Akiba et al. ......................... 548/314
3,846,441  11/1974  Mine et al. ......................... 548/314

OTHER PUBLICATIONS

*Chemical Abstracts*, 96:94933p, (1982), [Japan Kokai, 81, 111, 847, Mitsubishi, 9/3/1981].
*Chemical Abstracts*, 82:4174a, (1975), [Shalaby, A., et al., Indian J. Chem., 1974, 12, (6), 577-579].
*Chemical Abstracts*, 68:87240d, (1968), [Shirai, H., et al., Nagoya Shiritsu Daigaku Yakugakubu Kenkyu Nempo, 14, 63-65, (1966)].
*Chemical Abstracts*, 76:25168t, (1972), [Natarajan, P., Acta Pharm. Suecica, 1971, 8, (5), 537-540].
Conant, J., *The Chemistry of Organic Compounds*, Mac-Millan, New York, 1939, p. 264.
*Chemical Abstracts*, 67:82385a, (1967), [Eckstein, Z., et al., Rocz. Chem., 41, (3), 493-502, (1967)].
*Chemical Abstracts*, 64:8028d, (1966), [Konishi, K., Takeda Kenkyusho Nempo, 24, 246-249, (1965)].
*Chemical Abstracts*, 77:101615z, (1972), [Singhal, G., Swiss, 523, 008, 7/14/1972].

Primary Examiner—Richard A. Schwartz
Attorney, Agent, or Firm—Michael L. Dunn

[57] ABSTRACT

The invention describes a method for inhibiting the growth of pests comprising applying thereto a pesticidal amount of a compound of the formula

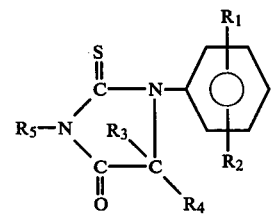

wherein $R_1$, and $R_2$ are independently hydrogen, substituted or unsubstituted lower alkyl, cycloalkyl, phenyl, or alkenyl, and halogen, amino or hydroxy groups, $R_3$ and $R_4$ are independently hydrogen or substituted or unsubstituted lower alkyl, $R_5$ is hydrogen, substituted or unsubstituted lower alkyl, cycloalkyl or phenyl, and naphthyl groups; pesticidal compositions containing at least one of said compounds; and novel thiohydantoin compounds having pesticidal activity.

11 Claims, No Drawings

PESTICIDAL THIOHYDANTOIN COMPOSITIONS

BACKGROUND OF THE INVENTION (A) Field of the Invention

This invention relates to pesticide compositions including fungicides, nematocides, herbicides and insecticides and more particularly relates to certain thiohydantoin compounds which, in accordance with the invention, have been found to have activity in inhibiting the growth of one or more pests.

(B) History of the Prior Art

Compounds having active pesticidal activity are known in nature, for example, certain microorganisms produce bactericidal antibiotic compositions and certain flowers contain insecticidal constituents. Men have for centuries utilized pesticidal compositions which initially were those obtained from nature, e.g. crushed pyrethrum flowers. Similarly, such naturally occurring pesticidal compositions are very good pesticides and continue to be used centuries after their initial discovery. Many pesticidal compositions which do not occur in nature have been chemically synthesized.

An ideal pesticide would be very specific to the pest being controlled, would have exceedingly low toxicity (including the carcinogenicity) to human beings and desirable life forms, would be highly active in controlling the pest, would be completely environmentally safe, and would be inexpensive due to its simplicity of manufacture from readily available low-cost materials. It is therefore clear that the ideal pesticide will probably never be obtained since specificity could almost always be better, toxicity could almost always be lower, the effectiveness could almost always be better, the environmental effects could almost always be less, and the cost could almost always be lower.

It is therefore highly desirable that entirely new classes of pesticide compositions be found.

Certain thiohydantoin compositions have been known in the prior art as color developers in photography, e.g. U.S. Pat. No. 2,551,134. There is no disclosure or suggestion in this patent concerning the possibility that such compositions or similar compositions would have pesticidal activity.

"Pesticide" and "Pesticidal Amounts" as used herein includes not only compounds and amounts thereof which will kill pests but which will inhibit their growth as, for example, by interfering with reproductive processes.

"Pest" as used herein means any nonvertebrate living organism which detrimentally attacks a desirable living organism including human beings or detrimentally attacks a desirable article or interferes with a desirable process. Examples of such pests include undesirable soil fungi such as pythium and rhizoactonia; weeds; certain insects and mites; certain nematodes such as rootknot and certain foilage fungi such as the mildews.

BRIEF DESCRIPTION OF THE INVENTION

In accordance with the invention, a method is provided for inhibiting the growth of the pest which comprises contacting the pest with a pesticidal quantity of a compound of the formula

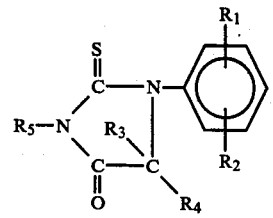

wherein $R_1$ and $R_2$ are independently hydrogen, substituted or unsubstituted lower alkyl, cycloalkyl, phenyl, or alkenyl, and halogen, amino or hydroxy groups, $R_3$ and $R_4$ are independently hydrogen or substituted or unsubstituted lower alkyl, $R_5$ is hydrogen, substituted or unsubstituted lower alkyl, cycloalkyl or phenyl, and naphthyl grouping. New pesticidal compositions are disclosed comprising at least one of the aforedescribed compounds as well as novel thiohydantoin compounds having pesticidal activity.

DETAILED DESCRIPTION OF THE INVENTION

As previously discussed, the method of the invention for inhibiting the growth of the pest comprises contacting the pest with the sufficient quantity of a compound having the generic formula:

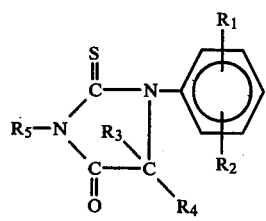

wherein $R_1$ and $R_2$ are independently hydrogen, substituted or unsubstituted lower alkyl, cycloalkyl, phenyl, or alkenyl, and halogen, amino or hydroxy groups, $R_3$ and $R_4$ are independently hydrogen or substituted or unsubstituted lower alkyl, $R_5$ is hydrogen, substituted or unsubstituted lower alkyl, cycloalkyl or phenyl, and naphthyl grouping; pesticidal compositions containing at least one of said compounds; and novel thiohydantoin compounds having pesticidal activity.

While essentially all of such compounds seem to have some activity against at least one pest, the particular activity and pest or pests whose growth is inhibited by the compound varies depending upon selection of the $R_1$, $R_2$, $R_3$, $R_4$ and $R_5$ groups in the generic formula. A slight change in any one of the R groups can dramatically affect the activity of the compound, i.e. the pest or pests against which the compound is effective and the quantity of compound required to inhibit the growth of the pest.

As previously discussed, the $R_1$ and $R_2$ groups may be independently at each occurrence hydrogen, substituted or unsubstituted lower alkyl, substituted or unsubstituted cycloalkyl, substituted or unsubstituted phenyl, alkenyl, halogen, amino or hydroxy groups. The most common $R_1$ and $R_2$ groups are hydrogen. "Substituted" as used herein means substituted with a halogen, amino, hydroxy, substituted and unsubstituted lower alkyl, substituted and unsubstituted phenyl and acyl. "Substituted" also includes the removal of substituents, especially hydrogen to form unsaturation. $R_3$ and $R_4$ are independently hydrogen, lower alkyl or substituted lower alkyl groups. $R_3$ and $R_4$ are most commonly hydrogen. $R_5$ is a hydrogen, lower alkyl, substituted lower alkyl, cycloalkyl, substituted cycloalkyl, phenyl, substituted phenyl or a naphthyl group.

As previously discussed, even slight changes, for example, in the $R_5$ group, often result in dramatic changes in the level of activity of the compound and in the types of pests against which the compound is effective. Changes of level of activity and effectiveness as a result of changes in the R groups does not appear to be predictable. For example, when $R_1$, $R_2$, $R_3$ ,and $R_4$ are hydrogen and $R_5$ is methyl, the compound has excellent activity against the nematode rootknot, very good activity against the morning glory weed and good activity against the foilage fungus anthracnose. The compound also shows varying levels of activity against other foilage fungi and weeds. Merely changing the $R_5$ group from a methyl to an ethyl lowers the activity of the compound as a herbicide against weeds. At the same time the activity against rootknot stays at essentially the same level and activity against the Mexican bean beetle increases. Changing the $R_5$ group to the phenyl group practically reduces its activity against rootknot but increases activity against the Mexican bean beetle.

As can be seen through the foregoing discussion, the method of the invention is very versatile since even slight changes in the R groups can result in dramatic changes in level of activity and in the pest against which the compound is affected. Prior art compositions often do not have such flexibility as a result of small changes in substituents.

The compounds used in the method of this invention can generally be prepared by methods known in the art such as by refluxing an appropriate N-phenyl glycine or glycinate with an appropriate substituted isothiocyanate as illustrated by the following equation:

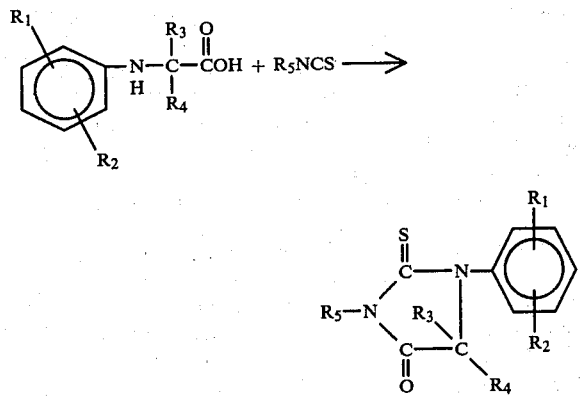

This method is furthur described in U.S. Pat. No. 2,551,134. Typical compounds coming within the method and pesticidal compositions of the invention include: 1-phenyl-2-thiohydantoin, 1-(3,5-dichlorophenyl)-2-thiohydantoin, 1-(4-chloromethylphenyl)-2-thiohydantoin, 1-(3-hydroxyphenyl)-2-thiohydantoin, 1-(2-amino phenyl)-2-thiohydantoin, 1-(5-nitro phenyl)-2-thiohydantoin, 1-phenyl-3-benzyl-2-thiohydantoin, 1-phenyl-3-benzyl-5-methyl-2-thiohydantoin, 1-(4-chloromethylphenyl)-3-methyl-5-ethyl-2-thiohydantoin, 1-phenyl-3(1-naphthyl)2-thiohydantoin, 1-phenyl-3-n-butyl-2-thiohydantoin, 1-phenyl-3-p-cyanophenyl-2-thiohydantoin, 1-phenyl-3-methyl-2-thiohydantoin, 1-phenyl-3- cyclohexyl-2-thiohydantoin, 1-phenyl-3-methyl-5-chloroethyl-2-thiohydantoin, 1-(4-trifluoromethylphenyl)-2-methyl-5-ethyl-2-thiohydantoin, 1-phenyl-3-ethyl-2-thiohydantoin, 1-phenyl-3-phenyl-2-thiohydantoin, 1-phenyl-3-propenyl-2-thiohydantoin, 1-phenyl-3-m-trifluoromethylphenyl-2-thiohydantoin, 1-phenyl-3-T-butyl-2-thiohydantoin, 1-phenyl-3-isopropyl-2-thiohydantoin, 1-phenyl-3(4-methylphenyl)-2-thiohydantoin, 1-phenyl-3(4-chlorophenyl)-2-thiohydantoin and the like.

The thiohydantoin compounds of the invention are generally biologically active as pesticides being one or more of herbicidal, fungicidal, insecticidal or nematocidal in activity and are generally useful for killing or inhibiting the growth of one or more species. As herbicides they have generally been found effective in either pre- or post-emergent applications. For pre-emergent control of selected undesired vegetation, the compounds are applied in herbicidal quantities to the environment or growth medium of the vegetation, e.g. soil infested with seeds and/or seedlings of such vegetation. Such application can inhibit the growth or kill the seeds, germinating seeds and seedlings. For post-emergent applications, the compounds of the present invention can be applied directly to the foilage and other plant parts. Similarly, for fungicidal, insecticidal and nematocidal application the compounds can be applied directly to the fungi, insects and/or nematodes or generally throughout the evironment or medium of the pests.

The thiohydantoin compounds of this invention may be used as solutions, emulsions, suspensions, dusts or the like. The form of application depends on the purpose to which the pesticide is being directed so as to insure an appropriate distribution thereof.

The thiohydantoin compounds of this invention may be used in the form of herbicidal, fungicidal, insecticidal or nematocidal compositions; such compositions containing conventional inert carriers, i.e., the liquid or solid agents normally associated with such biologically active compounds.

Suitable solid carriers include clays, silicates, synthetic hydrated silicon dioxides, resins, waxes, synthetic polymeric materials, carbon, sulfur and the like. Organic material such as walnut-shell flour, cottonseed hulls, wheat flour, wood flour or redwood-bark flour can also be used as solid carriers.

Suitable liquid carriers include water, alcohols, ketones, aromatic hydrocarbons, aliphatic hydrocarbons, chlorinated, aliphatic and aromatic hydrocarbons, petroleum fractions such as kerosene and the like.

In addition to the carrier, the pesticidal composition may contain a surface active agent. Such agents are those commonly known as wetting agents, dispersing agents and emulsifying agents and may be anionic, cationic or nonionic. Examples of suitable surface-active agents include alkyl-aryl sulfonates, alkyl sulfates containing more than ten carbon atoms, alkyl phenol/ethylene oxide condensates, sorbitan esters of fatty acids, alkyl amide sulphonates, ethyl oxide/fatty acid ester condensates and the like. The biologically active pesticidal composition may also contain other biologically active compounds, adjuvants, stabilizers, conditioners, fillers and the like.

The biologically active pesticidal composition, containing an inert carrier, surface active agent or other adjuvant, stabilizer, conditioner, filler or the like may be formulated as a wettable powder, a dust, granule, concentrate, solution, emulsifiable concentrate or the like.

The amount of the biologically active pesticidal compound necessary to kill or inhibit the growth of various fungi, insects, namatodes and/or vegetation will vary with the specific compound utilized, the species it is applied to, the type of formulation and the environmental conditions and the like at the time of application and during the period of activity.

Under a particular set of conditions for a particular pesticidal compound, in a particular formulation and for a particular biological activity, the appropriate amount of pesticidal compound may be readily ascertained.

The biologically active pesticidal composition may contain from about 0.001 to about 98 percent by weight of the pesticidal compound based upon the total weight of the composition.

Though the compounds of the instant invention display a broad range of pesticidal activity, various specific compounds display higher activity to various specific pests. Generally, the compounds of the instant invention have been found very effective on foliage fungi such as bean rust, bean powdery mildew, anthracnose and the like; soil fungi such as pythium, rhizoctonia and the like; vegetation such as the annuals including crabgrass, foxtail millet, Japanese millet and the like, the annual broadleafs such as morning glory, mustard, pigweed and the like; insects such as the Mexican bean beetle, southern armyworm, bean aphid, spotted mite, spider mite and the like; and nematodes such as the rootknot nematode and the like. It should be understood that though each of the compounds of the instant invention has at least some pesticidal activity, the type and extent of economically desirable activity varies from compound to compound in the selection of moieties represented by the various R groups. In many instances, even slight changes in the R groups may result in significant changes in the activity of a compound and the pests against which it is economically effective.

The following examples are meant to illustrate the invention. Unless otherwise indicated, all percentages are in parts by weight and all temperatures are degrees celsius.

EXAMPLE I 1-phenyl-3-benzyl-2-thiohydantoin

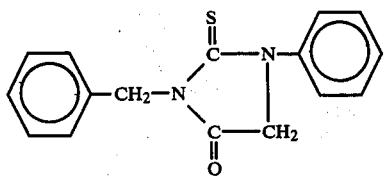

A mixture containing 30.2 g (0.2 M) of N-phenyl glycine, 37.2 g (0.25M) of benzylisothiocyanate and 80 ml of toluene was refluxed for 5 hours and allowed to stand at room temperature overnight. The product was washed with toluene and recrystallized from ethanol to produce 12 g (0.04 mole) of the above-identified product having a melting point of 103° C.

EXAMPLE II

Following the procedure of Example I about 0.025 moles of (A) 1-naphthylisothiocyanate, (B) n-butylisothiocyanate, and (C) p-cyanophenylisothiocyanate were separately refluxed with about 0.2 moles of N-phenyl glycine in toluene to produce the following respective products.

(A) 1-phenyl-3(1-naphthyl)-2-thiohydantoin

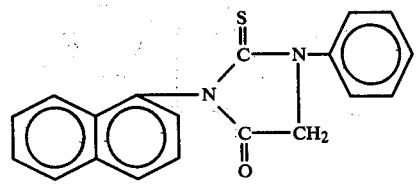

m.p. 210° C. - yield 45%

(B) 1-phenyl-3-n-butyl-2-thiohydantoin

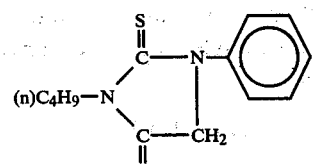

m.p. 48° C. - yield 32%

(C) 1-phenyl-3-p-cyanophenyl-2-thiohydantoin

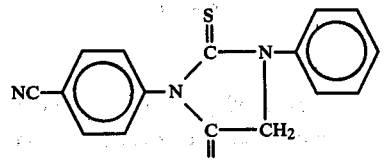

m.p. 197° C. - yield 34%

EXAMPLE III 1-phenyl-3-methyl-2-thiohydantoin

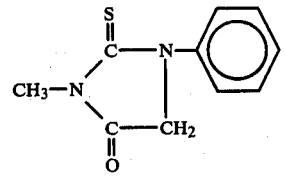

A mixture of ethyl-N-phenyl glycinate (26.9 g, 0.15 mole) was refluxed with methylisothiocyanate (16 g, 0.22 mole) for 5 hours and then allowed to stand at room temperature overnight. The reaction mixture was poured into 90 ml of ethanol and the suspension was collected by filtration and re-crystallized from ethanol to produce 17.89 g (0.086M) of the above-identified product having a melting point of 112° C.

EXAMPLE IV 1-phenyl-3-cyclohexyl-2-thiohydantoin

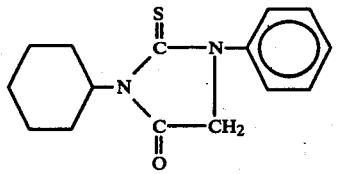

A mixture of N-phenyl glycine (15.1 g, 0.1M) and cyclohexylisothiocyanate (21.2 g, 0.15M) was heated at 100° C. for 8 hours and then allowed to stand at room temperature overnight. The reaction mixture was placed in about 50 ml of ethanol, collected by filtration and recrystallized from ethanol to produce 11 grams (0.047M) of the above-identified product having a melting point of 156° C.

EXAMPLE V 1-phenyl-3-phenyl-2-thiohydantoin

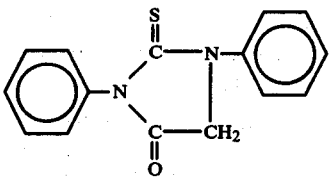

A mixture of N-phenyl glycine (7.5 gram, 0.05 mole) and phenylisothiocyanate (8 grams, 0.06 mole) was heated at 150° C. for 3 hours with stirring. The reaction mixture solidified, was ground up, and crystallized from toluene, twice, to produce 5 grams (37% yield) of the above-identified product having a melting point of about 214° C.

EXAMPLE VI 1-phenyl-3-ethyl-2-thiohydantoin

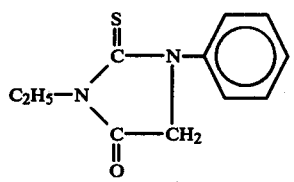

A mixture of ethyl-N-phenyl glycinate (17.9 grams, 0.1 mole) and ethylisothiocyanate (13.1 grams, 0.15 moles) was refluxed for 5 hours and allowed to stand overnight at room temperature (21° C.). The resulting solid was ground up and crystallized from ethanol to produce 12 grams (54% yield) of the above-identified product having a melting point of about 122° C.

EXAMPLE VII 1-phenyl-3-propenyl-2-thiohydantoin

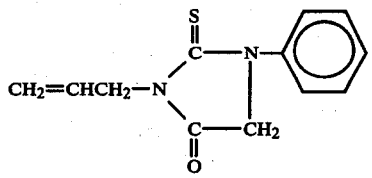

A mixture of N-phenyl glycine (15.1 grams, 0.1 moles) and allylisothiocyanate (12.0 grams, 0.12 moles) was refluxed for 6 hours and allowed to stand overnight at room temperature (21° C.). The reaction mixture became a solid mass which was ground and crystallized from ethanol using charcoal, 7.26 grams (31% yield) of the above-identified product was recovered having a melting point of about 74° C.

EXAMPLE VIII

A representative series of biological tests were selected which would indicate herbicidal, fungicidal, insecticidal and/or nematocidal activity on the part of the compounds tested. The compounds used in the invention were generally applied directly to the pests in the form of a solution and the biological effects of the compound tested were assessed visually and rated on an activity scale of 0-10 (0=no effect and 10=very strong pesticidal effect). The compounds were tested for pesticidal effect on bean rust, bean powdery mildew and nathracnose to assess foilage fungicidal activity; phthium and rhizoctonia to assess soil fungicidal activity; crabgrass, foxtail millet, Japanese millet, morning glory, mustard and pigweed to assess herbicidal activity; mexican bean beetle, southern armyworm and bean aphid to assess insecticidal activity; and, rootknot nematode to assess nematocidal activity. The results from the assessment of various compounds for various effects are set out in Table I.

TABLE I

| Compound | Pest | Activity |
|---|---|---|
| 1-phenyl-3-methyl-2-thiohydantoin | Powdery mildew | 1 |
| | Bean rust | 5 |
| | Anthracnose | 8 |
| | Morning Glory | 9 |
| | Mustard Weed | 7 |
| | Crabgrass | 2 |
| | Pigweed | 5 |
| | Rootknot Nematode | 10 |
| 1-phenyl-3-ethyl-2-thiohydantoin | Bean rust | 4 |
| | Morning Glory | 2 |
| | Pigweed | 4 |
| | Mexican bean beetle | 4 |
| | Rootknot nematode | 10 |
| 1-phenyl-3-phenyl-2-thiohydantoin | Powdery mildew | 2 |
| | Bean rust | 2 |
| | Anthracnose | 1 |
| | Mexican bean beetle | 8 |
| | Rootknot Nematode | 3 |
| 1-phenyl-3-propenyl-2-thiohydantoin | Powdery mildew | 2 |
| | Bean rust | 4 |
| | Anthracnose | 4 |
| | Morning Glory | 4 |
| | Pigweed | 3 |
| | Pythium | 2 |
| | Rhizoctonia | 3 |
| | Rootknot Nematode | 3 |
| 1-phenyl-3-cyclohexyl-2-thiohydantoin | Powdery mildew | 2 |
| | Bean rust | 2 |
| | Anthracnose | 2 |

TABLE I-continued

| Compound | Pest | Activity |
|---|---|---|
| | Morning Glory | 5 |
| | Mustard Weed | 2 |
| | Crabgrass | 3 |
| | Pigweed | 5 |
| | Rootknot Nematode | 3 |
| 1-phenyl-3-benzyl-2-thiohydantoin | Pythium | 8 |

What is claimed is:

1. A method for killing a pest selected from the group consisting of insects, mites, nematodes, and fungi or inhibiting the growth of a weeds selected from the group consisting of crabgrass, foxtail millet, Japanese millet and the annual broadleaf weeds, which comprises contacting the pest or weed with a pesticidal or inhibitory amount of a compound of the formula:

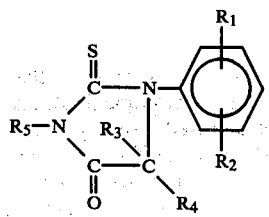

wherein $R_1$ and $R_2$ are independently hydrogen, lower alkyl, substituted lower alkyl, cyclo lower alkyl, phenyl, substituted phenyl, substituted cyclo lower alkyl, lower alkenyl, halogen, amino or hydroxy groups, $R_3$ and $R_4$ are independently hydrogen, lower alkyl or substituted lower alkyl groups and $R_5$ is a hydrogen, lower alkyl of at least two carbon atoms, substituted lower alkyl, cyclo lower alkyl, substituted cyclo lower alkyl, or naphthyl group wherein all substituents for substitution are selected from the group consisting of halogen, amino, and hydroxy.

2. The method of claim 1 wherein $R_3$ and $R_4$ are hydrogen.

3. The method of claim 2 wherein $R_1$ and $R_2$ are hydrogen.

4. The method of claim 3 wherein $R_5$ is naphthyl and the pest is downy mildew.

5. The method of claim 3 wherein $R_5$ is —CH$_2$—CH$_2$—CH$_2$—CH$_3$ and the pest is a mildew or anthracnose.

6. The method of claim 3 wherein $R_5$ is cycloalkyl and the pest is a weed.

7. The method of claim 3 wherein $R_5$ is ethyl and the pest is rootknot.

8. A method for killing insects which comprises contacting the insects with an insecticidal amount of a compound of the formula:

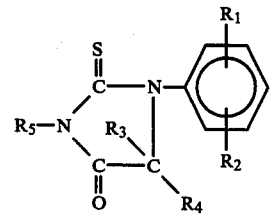

wherein $R_1$ and $R_2$ are independently hydrogen, lower alkyl, substituted lower alkyl, cyclo lower alkyl, phenyl, substituted phenyl, substituted cyclo lower alkyl, lower alkenyl, halogen, amino or hydroxy groups, $R_3$ and $R_4$ are independently hydrogen, lower alkyl or substituted lower alkyl groups and $R_5$ is phenyl wherein all substituents for substitution are selected from the group consisting of halogen, amino, and hydroxy.

9. A pesticidal composition suitable for killing pests selected from the group consisting of insects, mites, nematodes, and fungi or inhibiting the growth of weeds selected from the group consisting of crabgrass, foxtail millet, Japanese millet, and the annual broadleaf weeds comprising a carrier and a pesticidal or growth inhibiting amount of at least one compound of the formula:

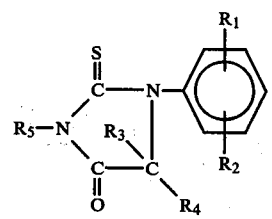

wherein $R_1$ and $R_2$ are independently hydrogen, substituted or unsubstituted lower alkyl, cyclo lower alkyl, phenyl, or lower alkenyl, and halogen, amino or hydroxy groups, $R_3$ and $R_4$ are independently hydrogen or substituted or unsubstituted lower alkyl, $R_5$ is hydrogen, substituted or unsubstituted lower alkyl of at least two carbon atoms, cyclo lower alkyl or naphthyl grouping wherein all substituents for substitution are selected from the group consisting of halogen, amino, and hydroxy.

10. A compound of the formula

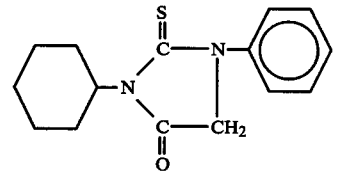

11. A compound of the formula

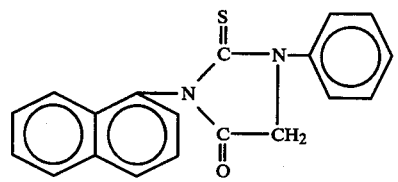

* * * * *